United States Patent [19]

Effland et al.

[11] Patent Number: 5,017,578
[45] Date of Patent: May 21, 1991

[54] N-HETEROARYL-PURIN-6-AMINES USEFUL AS ANALGESIC AND ANTICONVULSANT AGENTS

[75] Inventors: Richard C. Effland; Joseph T. Klein, both of Bridgewater; Larry Davis, Sergeantsville; Gordon E. Olson, Somerset, all of N.J.

[73] Assignee: Hoechst-Roussel Pharmaceuticals Inc., Somerville, N.J.

[21] Appl. No.: 363,837

[22] Filed: Jun. 9, 1989

[51] Int. Cl.$^5$ .................... A61K 31/52; A61K 31/70; C07D 473/34; C07H 19/173
[52] U.S. Cl. .................................. 514/266; 536/26; 514/46; 544/277
[58] Field of Search ..................... 544/277; 514/266

[56] References Cited

U.S. PATENT DOCUMENTS

| | | | |
|---|---|---|---|
| 3,016,378 | 1/1962 | Roch et al. | 544/277 X |
| 3,862,189 | 1/1975 | Schwender | 544/277 X |
| 4,514,405 | 4/1985 | Irmscher et al. | 514/46 |
| 4,657,897 | 4/1987 | Bristol et al. | 514/47 |
| 4,752,610 | 6/1988 | Efflund et al. | 514/343 |

OTHER PUBLICATIONS

Kanematsu, Chemical Abstracts, vol. 54: 5937g-i (1960).
Panagopoulos et al., Chemical Abstracts, vol. 63: 5646f-h–5647a-b (1965).
Lettre et al., Chemical Abstracts, vol. 65: 9542a-c (1966).
Fleysher et al., J. Med. Chem., vol. 12, pp. 1056-1061 (11/69).
Kelley et al., J. Med. Chem., vol. 29, pp. 1133-1134 (1986).
Katritzky, "Comprehensive Heterocyclic Chemistry", vol. 5, Part 4A, Pergamon Press (1984), pp. 592-598, 601-605.

*Primary Examiner*—Diana Rivers
*Attorney, Agent, or Firm*—Jerome Rosenstock

[57] ABSTRACT

This invention relates to a N-heteroaryl-purin-6-amine of the formula

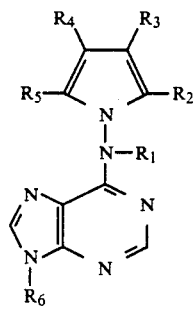

where $R_1$ is hydrogen, lower alkyl, and arylloweralkyl; $R_2$ and $R_3$ are independently hydrogen, lower alkyl or $R_2$ and $R_3$ taken together are aryl; $R_4$ and $R_5$ are independently hydrogen, lower alkyl, or $R_4$ and $R_5$ taken together are aryl; $R_6$ is hydrogen, lower alkyl, aryl, arylloweralkyl,

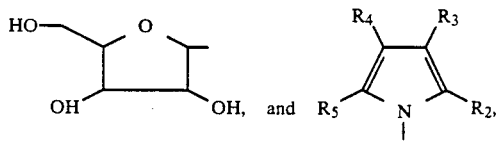

where $R_2$, $R_3$, $R_4$ and $R_5$ are as defined above, and the pharmaceutically acceptable acid addition salts thereof and where applicable the geometric and optical isomers and racemic mixtures thereof. The compounds of this invention display utility as analgesic and anticonvulsant agents.

47 Claims, No Drawings

N-HETEROARYL-PURIN-6-AMINES USEFUL AS ANALGESIC AND ANTICONVULSANT AGENTS

This invention relates to compounds of the formula

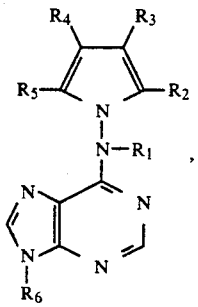

where $R_1$ is hydrogen, loweralkyl, and arylloweralkyl; $R_2$ and $R_3$ are independently hydrogen, loweralkyl or $R_2$ and $R_3$ taken together are aryl; $R_4$ and $R_5$ are independently hydrogen, lower alkyl or $R_4$ and $R_5$ taken together are aryl; and $R_6$ is hydrogen, lower alkyl, aryl, arylloweralkyl, where $R_2$, $R_3$, $R_4$ and $R_5$ are as defined above.

Throughout the specification and appended claims, a given chemical formula or name shall encompass all geometric and stereoisomers and racemic mixtures where such isomers and mixtures exist.

In the above definition, the term "lower" means the group it is describing contains from 1 to 6 carbon atoms. The term "alkyl" refers to a straight or branched chain hydrocarbon containing no unsaturation, e.g. methyl, ethyl, propyl, isopropyl, 2-butyl, neopentyl, n-hexyl, etc.; the term "arylloweralkyl" refers to a monovalent substituent which consists of an "aryl" group, e.g. phenyl, o-tolyl, m-methoxyphenyl, etc., as defined by the formula

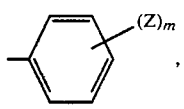

where Z is as defined below, and m is an integer of 1 to 3, linked through a loweralkylene group having its free valence bond from a carbon of the loweralkylene group, and having a formula of

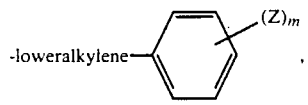

where Z is hydrogen, halogen, loweralkyl, loweralkoxy, $CF_3$, $NO_2$ and $NH_2$; the term "alkylene" refers to a bivalent radical of the lower branched or unbranched alkyl group it is derived from having valence bonds from two terminal carbons thereof, e.g. ethylene ($-CH_2CH_2-$), propylene ($-CH_2CH_2CH_2-$), isopropylene

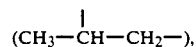

etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc., and the term "halogen" refers to a member of the halogen family consisting of fluorine, chlorine, bromine and iodine.

The compounds of the present invention are prepared in the following manner. The substituents, $R_1$ through $R_6$, Z and the integer m are as defined above unless indicated otherwise.

A substituted halo purine is selected having the formula

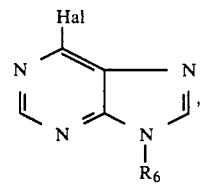

where Hal is a halogen selected from Cl, Br and iodine. Such substituted halo purines are well known or can be synthesized by conventional techniques well known by one of ordinary skill in the art. For example Compound II can be prepared following the teachings of Robins et al., *J. of Organic Chemistry*, Vol. 24, 1314 (1959) and the references cited therein, and Montgomery et al., *J. of the American Chemical Society*, Vol. 80, 409 (1958) and the references cited therein. Typically, for example, Compound II can be prepared by selecting a diamine of the formula

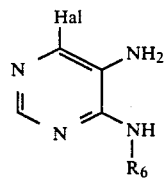

and reacting it with an orthoformate triester of the formula $CH(OR_7)_3$ (IV), where $R_7$ is lower alkyl. Compounds III are well known or are easily prepared by methods well known in the art, for example, such as by procedures described in Montgomery et al., *J. of the American Chemical Society*, Vol. 80, 409 (1958) and the references cited therein. Typically the reaction between Compounds III and IV is carried out in an acid solvent, e.g. glacial acetic acid, at a temperature of 20° to 120° C. for 1 to 24 hours to form Compound II.

Compound II is reacted with a substituted indolamine of the formula

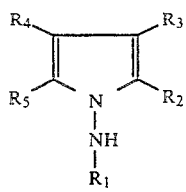

to form Compound I of the invention. Typically, the reaction of Compound II and Compound V is conducted in a polar solvent, e.g. ethanol, isopropanol, N-methyl-2-pyrrolidone, etc. at a temperature of 20° to 200° C. for 1 to 20 hours.

Substituted indolamines are well known or can be easily synthesized utilizing procedures well known in the art. Typically, for example, Compound V can be obtained by conventional alkylation of the substituted indolamine to introduce $R_1$ where $R_1$ is not hydrogen.

In an alternative embodiment, a nitropyrimidine diamine is selected having the formula

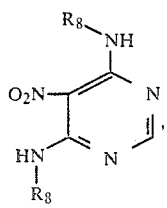

where $R_8$ is 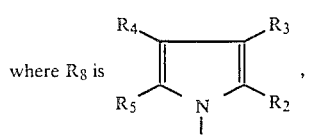, and where $R_2$, $R_3$, $R_4$ and $R_5$ are as defined above. Compound VI is prepared by reacting

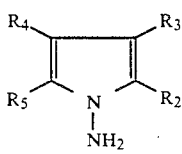

with a dichloronitropyrimidine having the formula

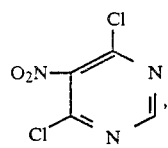

in the manner described in Boon et al., *Journal of the Chemical Society*, 96 (1951).

Compound VI is reduced in a conventional manner, e.g. with hydrogen at elevated pressures, such as 1 to 10 atmospheres, in the presence of a noble metal catalyst, e.g. $PtO_2$, Pd on carbon, in a suitable solvent, such as methanol, ethanol, etc., at a temperature of 20° to 80° C. for 1 to 24 hours to form Compound VII,

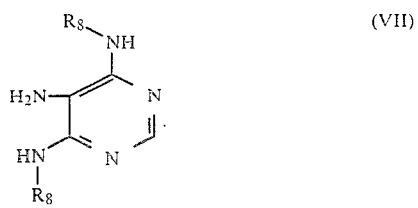

Compound VII in turn is reacted with the orthoformate triester, Compound IV, as described above, to form Compound I of the invention, where $R_6 = R_8$.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 95,729 (1957)]. The analgesic activity of some of the compounds expressed in terms of percent inhibition of writhing are given in TABLE I.

TABLE I

| Compound | Dose (subcutaneous) (mg/kg of body weight) | Inhibition of Writhing (%) |
| --- | --- | --- |
| N-(3-methyl-1H-indol-1-yl)-9H-purin-6-amine | 20.0 | 37 |
| N-(1H-pyrrol-1-yl)-9H-purin-6-amine | 20.0 | 37 |
| N-(9H-purin-6-yl)-9H-cabazol-9-amine | 20.0 | 55 |
| N-benzyl-N-(1H-pyrrol-1-yl)-9H-purin-6-amine | 20.0 | 37 |
| N-propyl-N-(1H-pyrrol-1-yl)-9H-purin-6-amine | 20.0 | 34 |
| 9-beta-D-ribofuranosyl-N-(1H-pyrrol-1-yl)-9H-purin-6-amine | 5.0 | 46 |
| 9-beta-D-ribofuranosyl-N-(1H-indol-1-yl)-9H-purin-6-amine | 0.08 | 50 |
| N-methyl-N-(1H-pyrrol-1-yl)-9-beta-D-ribofuranosyl-9H-purin-6-amine | 20.0 | 58 |
| N-(1H-pyrrol-1-yl)-N-propyl-9-beta-D-ribofuranosyl-9H-purin-6-amine | 20.0 | 42 |
| ibuprofen | 10.4 | 50 |

The analgesic relief of pain is achieved when the compounds of the invention are administered to a subject requiring such treatment at an effective oral, parenteral or intravenous dose of from 0.1 to 25 mg/kg of body weight per day. A preferred effective dose within this range is from about 1 to 10 mg/kg of body weight per day. It is to be understood, however, that for any particular subject, specific dosage regimens should be adjusted according to the individual need. It is further to be understood that the dosages set forth herein are examples only and that they do not to any extent, limit the scope of practice of the invention.

The compounds of the present invention are also useful as anticonvulsant agents for mammals, as determined by Woodbury, L. A. and Davenport, V. D. [Arch. Int. Pharmacodynam, 92, pp. 97–107 (1952)]. For example, 9-beta-D-ribofuranosyl-N-(1H-pyrrol-1-yl)-9H-purin-6-amine, and 9-beta-D-ribofuranosyl-N-(1H-indol-1-yl)-9H-purin-6-amine at an intraperitoneal dose of 18.0 and 35.8 mg/kg of body weight, respectively, produce a 50% protection from the effect of supramaximal electroshock. These data illustrate that compounds of the present invention are useful in treating convulsions in mammals when administered in amounts ranging from about 0.01 to about 150 mg/kg of body weight per day. A preferred effective dose within this range is from about 10 to 100 mg/kg of body weight. It is to be understood, however, that for any particular subject, specific dosage regimens should be adjusted according to the individual need. It is further to be understood that the dosages set forth herein are examples only and that they do not to any extent, limit the scope of practice of the invention.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of the N-heteroaryl-purin-6-amine derivative of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 1.0-300 milligrams of the N-heteroaryl-purin-6-amine derivative of the present invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the N-heteroaryl-purin-6-amine of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the N-heteroaryl-purin-6-amine derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetate, citrates or phosphates and agents for the adjustment of tonicity such as sodium chloride or dextrose. The parenteral preparation can be enclosed in ampules, disposable syringes or multiple dose vials made of glass or plastic.

Examples of some of the compounds include 9-phenyl-N-(1H-pyrrol-1-yl)-9H-purin-6-amine 9-phenyl-N-methyl-N-(1H-pyrrol-1-yl)-9H-purin-6-amine N-(1H-indol-1-yl)-9-phenyl-9H-purin-6-amine N-(1H-indol-1-yl)-N-methyl-9-phenyl-9H-purin-6-amine 9-(2-fluorobenzyl)-N-(1H-indol-1-yl)-N-methyl-9H-purin-6-amine 9-(2-chlorobenzyl)-N-(2-methyl-1H-indol-1-yl)-9H-purin-6-amine 9-(3,4-dimethoxybenzyl)-N-(3-methyl-1H-indol-1-yl)-9H-purin-6-amine 9-(1H-indol-1-yl)-N-(1H-pyrrol-1-yl)-9H-purin-6-amine 9-(1H-indol-1-yl)-N-methyl-N-(1H-pyrrol-1-yl)-9H-purin-6-amine and 9-beta-D-ribofuranosyl-N-(1H-indol)-1-yl)-N-methyl-9H-purin-6-amine.

The following examples are for illustrative purposes and are not to be construed as limiting the invention disclosed herein. All temperatures are given in degrees centigrade unless indicated otherwise.

EXAMPLE 1 a. 3-Methyl-1H-indol-1-amine

To 700 ml of dimethylformamide (DMF) was dissolved 3-methyl indole (50 g., 0.38 mole) and the solution was cooled to 4° C. with an ice-salt bath. Milled KOH (121.8 g, 5 equivalents) was added to the mixture, portionwise, keeping the internal temperature at 4° C. Hydroxylamine-O-sulfonic acid (56.54 g, 0.5 mole) was added portionwise over two hours, keeping the internal temperature between 4°-9° C. After the addition was complete, the reaction was stirred for one hour at about 9° C. The mixture was then poured into 1.4 l of ice-water to bring the total volume to 2.4 l. The aqueous layer was then extracted three times with ethyl acetate, the organics combined, washed with water and dried (saturated NaCl, anhydrous MgSO$_4$). After filtering, the solvent was evaporated to yield an oil (64.45 g) which was eluted with 50% hexanes in dichloromethane, and then dichloromethane. The desired fractions were evaporated to yield a solid of 3-methyl-1H-indol-1-amine, 32.4 g (58.4%) m.p. 60°-63° C.

b. N-(3-Methyl-1H-indol-1-yl)-9H-purin-6-amine

To a mixture of 6-chloropurine (5.0 g, 0.032 mole) and 1 ml ether-HCl in 150 ml of isopropanol was added 3-methyl-1H-indol-1-amine (45% pure, 9.77 g, 0.030 mole) in 50 ml of isopropanol and this mixture was heated to 80° C. and stirred for four hours. After cooling, the mixture was poured into water and basified with Na$_2$CO$_3$ (aqueous), extracted with ethyl acetate, washed with water and dried (saturated NaCl, anhydrous MgSO$_4$). After filtering, the solvent was evaporated to yield a solid (8.5 g), which was triturated with dichloromethane (DCM) to yield a solid (3.25 g). This material was then recrystallized in methanol to yield N-(3-methyl-1H-indol-1-yl)-9H-purin-6-amine, 2.2 g (28%) m.p. 319°–321° C. (decomp.).

Analysis: Calculated for $C_{14}H_{12}N_6$: 63.64% C; 4.55% H; 31.81% N. Found: 63.36% C; 4.61% H; 31.43% N.

EXAMPLE 2

N-(1H-Pyrrol-1-yl)-9H-purin-6-amine

A solution of 6-chloropurine (5 g, 32 mmole) and 1H pyrrol-1-amine (3 g, 36 mmole) in 75 ml isopropanol stirred one hour at reflux then was cooled, diluted with ether and filtered to give 8 g of a solid, d.250° C. Four grams were dissolved in methanol, basified with triethylamine and the precipitate collected and dried to give 3 g of a solid, m.p.>260° C. This solid was recrystallized from methanol to give 2.6 g (71%) of N-(1H-pyrrol-1-yl)-9H-purin-6-amine d.310° C.

Analysis: Calculated for $C_9H_8N_6$: 53.99% C; 4.03% H; 41.99% N. Found: 53.67% C; 3.92% H; 41.64% N.

EXAMPLE 3 a. 9H-Carbazol-9-amine

Into 250 ml of dimethylformamide was dissolved 25 g of carbazole. This solution was cooled with an ice-salt bath and 42 g of potassium hydroxide was added portionwise. To this mixture was added hydroxylamine-O-sulfonic acid. After two hours the mixture was stirred with water and extracted with ethyl acetate. The organic extracts were washed with water and brine. After filtering the solvent was evaporated and the residue was eluted with 25% dichloromethane in hexane on a silica column to yield 9.5 g of a mixture of carbazole and 9H-carbazol-9-amine.

b. N-(9H-Purin-6-yl)-9H-carbazol-9-amine

A solution of 6 chloropurine (4 g, 25 mmole) and 9H-carbazol-9-amine (4.6 g, 25 mmole) in 100 ml isopropanol acidified with ether-HCl was stirred at reflux for one hour then was cooled, diluted with ether and filtered to give 8 g of a solid, m.p. 210°–215° C. This solid was dissolved in methanol, basified with triethylamine and the precipitate collected and dried to give 6 g of a solid. The solid was recrystallized from methanol to give 4 g of N-(9H-purin-6-yl)-9H-carbazol-9-amine, d 284°–286° C.

Analysis: Calculated for $C_{17}H_{12}N_6$: 67.98% C; 4.03% H; 27.99% N. Found: 67.64% C; 4.14% H; 27.94% N.

EXAMPLE 4 a. N-Benzyl-1H-pyrrol-1-amine

To a mixture of 1H-pyrrol-1-amine (9.2 g, 0.112 mole) and $NaHCO_3$ (15 g, 0.19 mole) in 50 ml dichloromethane (DCM) at 0° C., was added ethyl chloroformate (11.4 ml, 0.12 mole) in fifteen minutes. After stirring at 0° C. for one hour, then at ambient temperature for four hours, the mixture was filtered and the filtrate was washed with water, then dried (saturated NaCl solution, anhydrous $MgSO_4$). After filtering, the solvent was evaporated to give a solid, 17 g (95%), m.p. 60°–61° C., of N-(1H-pyrrol-1-yl) carbamic acid ethyl ester. To a solution of N-(1H-pyrrol-1-yl) carbamic acid ethyl ester (9.0 g, 0.058 mole) in 30 ml tetrahydrofuran (THF) at 5° C., was added potassium t-butoxide (7.8 g, 0.07 mole) and the mixture was stirred at 5° C. for one hour. To this mixture was added benzyl bromide (7.1 ml, 0.06 mole) in ten minutes, and the mixture stirred at 5° C. for one hour, then at ambient temperature for four hours. This mixture was poured into 100 ml ice-water, stirred for five minutes, then extracted with ethyl acetate. The organic layer was washed with water, then dried (saturated NaCl, anhydrous $MgSO_4$). After filtering, the solvent was evaporated to an oil, 14 g (98%) of N-benzyl-N-(1H-pyrrol-1-yl) carbamic acid ethyl ester. To a solution of N-benzyl-N-(1H-pyrrol-1-yl) carbamic acid ethyl ester (14 g, 0.058 mole) in 15 ml ethylene glycol was added a solution of NaOH (5 g, 0.12 mole) in 10 ml water. After stirring at 120° C. for seven hours, the mixture was poured into 100 ml of iced-water, stirred for five minutes, then extracted with ethyl acetate. The organic layer was washed with water, then dried (saturated NaCl, anhydrous $MgSO_4$). After filtering, the solvent was evaporated to an oil, which was vacuum distilled to give an oil, 7.4 g (74%) of N-benzyl-1H-pyrrol-1-amine, b.p. 85°–125° C./1 mm; m.p. 39°–41° C.

b. N-Benzyl-N-(1H-pyrrol-1-yl)-9H-purin-6-amine

To a solution of 6-chloropurine (5.0 g, 0.032 mole) in 100 ml isopropanol, was added 1 ml ethereal-HCl, followed by a solution of N-benzyl-1H-pyrrol-1-amine (6.9 g, 0.04 mole) in 50 ml isopropanol. After stirring at 90° C. for four hours, the mixture was cooled, poured into 1 L iced-water, pH adjusted to 10 with $Na_2CO_3$, then extracted with ethyl acetate. The organic layer was washed with water, then dried (saturated NaCl, anhydrous $MgSO_4$). After filtering, the solvent was evaporated to a solid, 10 g, which was triturated with ether and dried to give 7.9 g of a solid, d.215° C. This material was recrystallized from methanol to give 4.3 g (46%) of N-Benzyl-N-(1H-pyrrol-1-yl)-9H-purin-6-amine d.216° C.

Analysis: Calculated for $C_{16}H_{14}N_6$: 66.19% C; 4.86% H; 28.95% N. Found: 65.74% C; 4.93% H; 28.85% N.

EXAMPLE 5 a. N-Methyl-1H-pyrrol-1-amine

To a solution of N-(1H-pyrrol-1-yl) carbamic acid ethyl ester (9.0 g, 0.058 mole) in 30 ml tetrahydrofuran (THF) at 5° C., was added potassium t-butoxide (7.8 g, 0.07 mole), and the mixture was stirred at 5° C. for one hour. To this was added methyl iodide (4.1 ml, 0.065 mole) in ten minutes, and the mixture stirred at 5° C. for one hour, then at ambient temperature for four hours. The mixture was poured into 100 ml ice water, stirred for five minutes, then extracted with ethyl acetate. The organic layer was washed with water, then dried (saturated NaCl, anhydrous $MgSO_4$). After filtering, the solvent was evaporated to an oil, 9.4 g (93%), of N-methyl-N-(1H-pyrrol-1-yl) carbamic acid ethyl ester. To a solution of N-methyl-N-(1H-pyrrol-1-yl) carbamic acid ethyl ester (9.4 g, 0.055 mole) in 15 ml ethylene glycol, was added a solution of NaOH (0.12 mole, 5 g) in 10 ml water. After stirring at 120° C. for four hours, the mixture was poured into 100 ml ice water, stirred for five minutes, then extracted with ethyl acetate. The organic layer was washed with water, then dried (saturated NaCl, anhydrous $MgSO_4$), filtered and then evaporated to an oil which was vacuum distilled to give N-methyl-1H-pyrrol-1-amine 4.3 g, (81%), b.p. 32°–5° C./1 mm.

b. N-Methyl-N-(1H-pyrrol-1-yl)-9H-purin-6-amine

To a solution of 6-chloropurine (4.7 g, 0.03 mole) in 100 ml isopropanol, was added 1 ml of ethereal-HCl; followed by a solution of N-methyl-1H-pyrrol-1-amine (3.8 g, 0.04 mole) in 50 ml isopropanol. After stirring at 90° C. for three hours, the mixture was cooled, poured into 1 l iced-water, the pH adjusted to 10 with Na$_2$CO$_3$ and then extracted with ethyl acetate. The organic layer was washed with water, then dried (saturated NaCl, anhydrous MgSO$_4$). After filtering, the solvent was evaporated to a solid, 3.1 g, which was triturated with ether and dried to give 2.7 g of a solid d.215° C. This material was recrystallized from methanol to give 2.2 g (32%) of N-Methyl-N-(1H-pyrrol-1-yl)-9H-purin-6-amine d.218° C.

Analysis: Calculated for C$_{16}$H$_{10}$N$_6$: 56.06% C; 4.71% H; 39.23% N. Found: 55.80% C; 4.79% H; 39.24% N.

EXAMPLE 6 a. N-Propyl-1H-pyrrol-1-amine

To 1H-pyrrol-1-amine (82 g, 1.0 mole) in 500 ml of dichloromethane (DCM) was added NaHCO$_3$ (150 g) and this mixture was cooled to ice bath temperature. To this was added ethyl chloroformate (104 ml, 1.1 mole) dropwise, and the mixture was stirred at ice bath temperature for one hour, then at room temperature for four hours. The mixture was filtered and the filtrate was washed with water and dried (saturated NaCl, anhydrous MgSO$_4$). After filtering, the solvent was evaporated to yield a solid 154 g (100%), m.p. 59°–61° C. This material was then dissolved in 500 ml of tetrahydrofuran (THF) and this was cooled to ice bath temperature. Potassium t-butoxide (139.13 g, 1.24 mole) was added portionwise, to the mixture and the reaction was stirred at ice bath temperature for one hour. A solution of iodopropane in 20 ml of THF was added, dropwise, and the mixture was stirred at room temperature for five hours. The mixture was then poured into water and extracted twice with ethyl acetate. The combined organics were washed with water and dried (saturated NaCl, anhydrous MgSO$_4$). After filtering, the solvent was evaporated to yield an oil 178.55 g (87.6%). This material was dissolved in ethylene glycol (250 ml) and to this was added NaOH (43.69 g, 1.09 mole) in 200 ml of H$_2$O. This mixture was heated to 120° C. and stirred vigorously for seven hours. The mixture was then poured into water and extracted three times with ethyl acetate. The combined organics were washed with water and dried (saturated NaCl, anhydrous MgSO$_4$). After filtering, the solvent was evaporated to yield an oil (158 g) which was distilled to yield an oil, 102 g (90%), of N-propyl-1H-pyrrol-1-amine.

b. N-Propyl-N-(1H-pyrrol-1-yl)-9H-purin-6-amine

To a stirring solution of 6-chloropurine (5.0 g, 0.032 mole) in 50 ml isopropanol and 1 ml ethereal-HCl was added N-propyl-1H-pyrrol-1-amine (3.72 g, 0.030 mole) in 20 ml of isopropanol. The mixture was heated to 80° C. and stirred for four hours. The mixture was poured into water, basified with Na$_2$CO$_3$ (aq.) and extracted with ethyl acetate. The organic layer was washed with water and dried (saturated NaCl, anhydrous MgSO$_4$). After filtering, the solvent was evaporated to yield a solid (6.5 g) which was triturated with ether to yield a solid (4.8 g). This material was then recrystallized from ethyl acetate/ether (1:5) to yield a solid 3.0 g (41%) of N-propyl-N-(1H-pyrrol-1-yl)-9H-purin-6-amine, m.p. 181°–183° C.

Analysis: Calculated for C$_{12}$H$_{14}$N$_6$: 59.49% C; 5.82% H; 34.69% N. Found: 59.44% C; 5.82% H; 34.76% N.

EXAMPLE 7

9-(2-Fluorobenzyl)-N-(1H-indol-1-yl)-9H-purin-6-amine

A solution of 6-chloro-9-(2-fluorobenzyl)-9H-purine (3.6 g, 13.7 mmole) (which is prepared by procedures described in Kelly et al, *J. of Medicinal Chemistry*, Vol. 29, 1133 (1986) and references cited therein) and 1H-indol-1-amine (3 g, 22.7 mmole) in 100 ml isopropanol was stirred one hour at reflux then was cooled, stirred with water, basified with sodium carbonate and extracted with ethyl acetate. The organic extract was washed with water and saturated sodium chloride, was dried (anhydrous MgSO$_4$), filtered and evaporated to 6 g of a solid. The solid was purified by flash chromatography (silica, 10% ethyl acetate in dichloromethane) to give 4.2 g of a solid. This solid was decolorized by triturating with ether-petroleum ether to give 3.4 g (69%) of 9-(2-fluorobenzyl)-N-(1H-indol-1-yl)-9H-purin-6-amine, m.p. 236°–238° C.

Analysis: Calculated for C$_{20}$H$_{15}$FN$_6$: 67.03% C; 4.22% H; 23.44% N. Found: 67.21% C; 4.28% H; 23.31% N.

EXAMPLE 8 a. N-(1H-Indol-1-yl)-N-propylamine

To a suspension of NaHCO$_3$ (50 g, 0.7 mole) in 100 ml dichloromethane (DCM) was added a solution of 1H-indol-1-amine (36 g, 0.27 mole) in 200 ml DCM. After cooling to 0° C. with an ice bath, a solution of ethyl chloroformate (29 ml, 0.30 mole) in 50 ml DCM was added over a period of thirty minutes. After stirring at ambient temperature for three hours, the mixture was filtered, and the filtrate washed with water, then dried (saturated NaCl, anhydrous MgSO$_4$). After filtering, the solvent was evaporated to an oil which was eluted on a silica gel column with DCM, via high performance liquid chromatography (HPLC) to give N-(1H-indol-1-yl) carbamic acid ethyl ester, 33.6 g (61%) as an oil. To a cold solution of N-(1H-indol-1-yl) carbamic acid ethyl ester (15 g, 0.07 mole) in 100 ml tetrahydrofuran, was added potassium t-butoxide (9 g, 0.08 mole), and the mixture stirred at 5° C. for one hour. To this was added 1-bromopropane (7.3 ml, 0.08 mole), and the mixture stirred at ambient temperature for five hours. The mixture was poured into 300 ml iced-water, stirred for five minutes, then extracted with ethyl acetate. The organic layer was washed with water, then dried (saturated, NaCl, anhydrous MgSO$_4$). After filtering, the solvent was evaporated to give N-(1H-indol-1-yl)-N-propylcarbamic acid ethyl ester as an oil, 16.5 g (91%). To a solution of N-(1H-indol-1-yl)-N-propylcarbamic acid ethyl ester (16.5 g, 0.067 mole) in 35 ml ethylene glycol, was added a solution of NaOH (10 g, 0.25 mole) in 30 ml water. After stirring at 120° C. for four hours, the mixture was poured into 300 ml ice water, stirred for five minutes, then extracted with ethyl acetate. The organic layer was washed with water, then dried (saturated NaCl, anhydrous MgSO$_4$). After filtering, the solvent was evaporated to give N-(1H-indol-1-yl)-N-propylamine, 9.0 g (78%) as an oil.

b. N-(1H-Indol-1-yl)-N-propyl-9H-purin-6-amine

To a solution of 6-chloropurine (5.0 g, 0.032 mole) in 50 ml 1-methyl-2-pyrrolidinone, was added 1 ml ethereal-HCl; followed by a solution of N-(1H-indol-1-yl)-N-propylamine (5.2 g, 0.030 mole) in 50 ml 1-methyl-2-pyrrolidinone. After stirring at 120° C. for six hours, the mixture was cooled, poured into 500 ml water and stirred for five minutes, pH adjusted to 10 with $Na_2CO_3$; then extracted with ethyl acetate. The organic layer was washed with water, then dried (saturated NaCl, anhydrous $MgSO_4$). After filtering, the solution was evaporated to an oil, about 8 g, which was eluted on a silica gel column with ethyl acetate via high pressure liquid chromatography. The desired fractions were combined, then evaporated to yield 2.2 g (25%) of N-(1H-indol-1-yl)-N-propyl-9H-purin-6-amine, m.p. 90°-5° C.

Analysis: Calculated for $C_{16}H_{16}N_6$: 65.74% C; 5.52% H; 28.75% N. Found: 65.67% C; 5.50% H; 28.20% N.

EXAMPLE 9 a.
6-Chloro-4-[N-(1H-pyrrol-1-yl)]-4,5-pyrimidinediamine

A solution of 4,6-dichloro-5-pyrimidinamine (which is prepared by methods described in Robins, *J. Org. Chem.* 19 930 (1954)), (5 g, 30.5 mmole) and 1H-pyrrol-1-amine (12 g, 146 mmole) in 150 ml isopropanol and 2 ml ether-HCl was stirred five hours at reflux, then was cooled, filtered and evaporated to an oil. This oil was purified by flash chromatography (silica, 5% ethyl acetate in dichloromethane) to give 10 g product with aminopyrrole. This was combined with 2 g product obtained from a previous condensation, triturated with petroleum ether and purified with high pressure liquid chromatography (silica, 10% ethyl acetate in dichloromethane) to give 4.8 g of an oil. This oil was crystallized by triturating with hexane to give 4 g (44%) of a solid, m.p. 100° C. This solid was recrystallized from ether-hexane to give 3 g (33%) of 6-chloro-4-[N-(1H-pyrrol-1-yl)]-4,5-pyrimidinediamine, m.p. 130°-132° C.

Analysis: Calculated for $C_8H_8ClN_5$: 45.83% C; 3.85% H; 33.41% N. Found: 45.71% C; 3.86% H; 33.16% N.

b. 6-Chloro-9-(1H-pyrrol-1-yl)-9H-purine

A solution of 6-chloro-4-[N-(1H-pyrrol-1-yl)]-4,5-pyrimidinediamine (5.6 g, 27 mmole) in 27 ml triethyl orthoformate and 10 ml glacial acetic acid was stirred thirty minutes at reflux, then was cooled and evaporated. The product was purified by flash chromatography (silica, 10% ethyl acetate in dichloromethane) to give 5.4 g (92%) of a solid, m.p. 204°-206° C. 2.4 g sublimed (130°-140° C./0.01 mm) to give 2.3 g of 6-chloro-9-(1H-pyrrol-1-yl)-9H-purine, m.p. 204°-206° C.

Analysis: Calculated for $C_9H_6ClN_5$: 49.20% C; 2.75% H; 31.89% N. Found: 49.06% C; 2.72% H; 31.98% N.

EXAMPLE 10

9-(1H-Pyrrol-1-yl)-N-(1H-pyrrol-1-yl)-9H-purin-6-amine

A solution of 6-chloro-9-(1H-pyrrol-1-yl)-9H-purine (3 g, 14 mmole) and 1H-pyrrol-1-amine (2 g, 24 mmole) in 100 ml isopropanol was warmed on a steam bath for thirty minutes then was evaporated, stirred with water, basified with sodium carbonate and extracted with ethyl acetate. The organic extract was washed with water and saturated sodium chloride, was dried (anhydrous $MgSO_4$), filtered and evaporated to yield 5 g of a solid. This solid was purified by flash chromatography (silica, 10% ethyl acetate in dichloromethane) to give 4 g of a solid, m.p. 200°-205° C. This solid was recrystallized from ethyl acetate to give 1.7 g (47%) of 9-(1H-pyrrol-1-yl)-N-(1H-pyrrol-1-yl)-9H-purin-6-amine, m.p. 230°-232° C.

Analysis: Calculated for $C_{13}H_{11}N_7$: 58.86% C; 4.18% H; 36.96% N. Found: 58.67% C; 4.18% H; 37.03% N.

EXAMPLE 11

6-Methylamino-9-(1H-pyrrol-1-yl)-9H-purine hydrochloride

A solution of 6-chloro-9-(1H-pyrrol-1-yl)-9H-purine (3 g, 14 mmole) in 25 ml methanol and 25 ml 40% aqueous methylamine was warmed on a steam bath for thirty minutes then was cooled and evaporated. The residue was purified by flash chromatography (silica, 50% ethyl acetate in dichloromethane) to give 2.9 g of a solid, m.p. 174°-176° C. This solid was converted to the hydrochloride salt by adding ethereal-HCl to a methanol solution to give 2.4 g (70%) of 6-methylamino-9-(1H-pyrrol-1-yl)-9H-purine hydrochloride, d290° C.

Analysis: Calculated for $C_{10}H_{10}N_6 \cdot HCl$: 47.91% C; 4.42% H; 33.52% N. Found: 47.90% C; 4.37% H; 33.67% N.

EXAMPLE 12

9-(2-Fluorobenzyl)-N-(1H-pyrrol-1-yl)-9H-purin-6-amine

A solution of 6-chloro-9-(2-fluorobenzyl)-9H-purine (4.2 g, 16 mmole) and 1H-pyrrol-1-amine (3 g, 36 mmole) in 25 ml isopropanol was stirred at reflux for thirty minutes then was cooled, diluted with water, basified with sodium carbonate and extracted with dichloromethane. The organic extract was washed with water and saturated sodium chloride, was dried (anhydrous $MgSO_4$), filtered and evaporated to 6 g of a solid. The solid was purified by flash chromatography (silica, 15% ethyl acetate in dichloromethane) to give 4.5 g of 9-(2-fluorobenzyl)-N-(1H-pyrrol-1-yl)-9H-purin-6-amine, m.p. 204°-206° C.

Analysis: Calculated for $C_{16}H_{13}FN_6$: 62.32% C; 4.25% H; 27.26% N. Found: 62.15% C; 4.21% H; 27.30% N.

EXAMPLE 13

9-(2-Fluorobenzyl)-N-methyl-N-(1H-pyrrol-1-yl)-9H-purin-6-amine

A solution of 6-chloro-9-(2-fluorobenzyl)-9H-purine (4 g, 15 mmole) and N-(1H-pyrrol-1-yl)-methylamine (3 g, 31 mmole) in 25 ml isopropanol stirred two hours at 90° C., then was cooled, evaporated, basified with sodium carbonate and extracted with ethyl acetate. The organic extract was washed with water and saturated sodium chloride, was dried (anhydrous $MgSO_4$), filtered and evaporated to 6 g of an oil. The oil was purified by flash chromatography (silica, 10% ethyl acetate in dichloromethane) to give 4.5 g of a solid. The solid was recrystallized from ethyl acetate-petroleum ether to give 3.7 g (75%) of 9-(2-fluorobenzyl)-N-methyl-N-(1H-pyrrol-1-yl)-9H-purin-6-amine, m.p. 147°-149° C.

Analysis: Calculated for $C_{17}H_{15}FN_6$: 63.34% C; 4.69% H; 26.07% N. Found: 62.96% C; 4.66% H; 26.06% N.

EXAMPLE 14 a.
N,N'-bis(1H-Indol-1-yl)-5-nitro-4,6-pyrimidinediamine

A solution of 4,6-dichloro-5-nitropyrimidine (8 g, 41 mmole) and 1H-indol-1-amine (12 g, 91 mmole) in 100 ml ethanol was warmed on a steam bath for thirty minutes then was cooled, diluted with ether and filtered to give 8 g of a solid, 250° C. (dec.). Four grams were purified by flash chromatography (silica, dichloromethane) to give 3.5 g of a solid. The solid was recrystallized from acetone-ether to give 2.2 g (28%) of N,N'-bis(1H-indol-1-yl)-5-nitro-4,6-pyrimidinediamine, 258°–260° C. (dec.).

Analysis: Calculated for $C_{20}H_{15}N_7O_2$: 62.33% C; 3.92% H; 25.44% N. Found: 62.13% C; 3.85% H; 25.50% N.

b.
9-(1H-Indol-1-yl)-N-(1H-indol-1-yl)-9H-purin-6-amine

A mixture of N,N'-bis(1H-indol-1-yl)-5-nitro-4,6-pyrimidinediamine (4 g, 10.4 mmole) in 250 ml ethanol containing 200 mg $PtO_2$ was hydrogenated at 55 psi for four hours, then was filtered and evaporated to 4 g of a solid, m.p. 198°–200° C. A solution of 4-[N-(1H-indol-1-yl)-6-[N-(1H-indol-1-yl)]-4,5,6-pyrimidinetriamine (6 g, 17 mmole) in 25 ml triethyl orthoformate and 9 ml glacial acetic acid stirred one hour at 90° C. then was cooled and evaporated. The residue was dissolved in ether and washed with water, sodium carbonate solution, again with water and saturated sodium chloride, then was dried (anhydrous $MgSO_4$), filtered and evaporated to 6 g of an oil. This oil was purified by flash chromatography to give 4 g of a solid. This solid was recrystallized twice from ethyl acetate-petroleum ether to give 2.8 g (49% overall) of 9-(1H-indol-1-yl)-N-(1H-indol-1-yl)-9H-purin-6-amine, m.p. 196°–198° C.

Analysis: Calculated for $C_{21}H_{15}N_7$: 69.03% C; 4.14% H; 26.83% N. Found: 69.06% C; 4.09% H; 26.94% N.

EXAMPLE 15

9-β-D-Ribofuranosyl-N-(1H-pyrrol-1-yl)-9H-purin-6-amine

A mixture of 6-chloropurine riboside (3 g, 10.5 mmole), 1H-pyrrol-1-amine (2.6 g, 31.5 mmole) and calcium carbonate (2.1 g, 21 mmole) in 150 ml ethanol was stirred two hours at reflux, then was cooled, filtered, evaporated with 25 g silica, eluted with ethyl acetate and then 10% methanol in dichloromethane via flash chromatography to give 3.5 g of a solid, m.p. 125° C. The solid was combined with 2.1 g product obtained from another condensation and purified by high pressure liquid chromatography (silica, 10% methanol in dichloromethane) to give 4 g of a solid. This solid was recrystallized from acetonitrile to give 3.6 g (62%) of 9-β-D-ribofuranosyl-N-(1H-pyrrol-1-yl)-9H-purin-6-amine, m.p. 193°–195° C.

Analysis: Calculated for $C_{14}H_{16}N_6O_4$: 50.60% C; 4.85% H; 25.29% N. Found: 50.63% C; 4.81% H; 25.38% N.

EXAMPLE 16

9-β-D-Ribofuranosyl-N-(1H-indol-1-yl)-9H-purin-6-amine

A solution of 6-chloropurine riboside (5 g, 17.4 mmole) and 1H-indol-1-amine (5 g, 37.8 mmole) in 250 ml absolute ethanol containing calcium carbonate (5 g, 50 mmole) was stirred at reflux for four hours, then was cooled, filtered and evaporated to 11 g of a solid. This solid was purified by high pressure liquid chromatography (silica, 10% methanol in dichloromethane) to give 5.5 g of a solid. This solid was recrystallized twice from acetonitrile to give 3.3 g (49%) of 9-β-D-ribofuranosyl-N-(1H-indol-1-yl)-9H-purin-6-amine, m.p. 155° C.

Analysis: Calculated for $C_{18}H_{18}N_6O_4$: 56.53% C; 4.74% H; 21.98% N. Found: 56.12% C; 4.72% H; 21.75% N.

EXAMPLE 17

N-Methyl-N-(1H-pyrrol-1-yl)-9-β-D-ribofuranosyl-9H-purin-6-amine

To 100 ml absolute ethanol was added 6-chloropurine riboside (5.0 g, 0.017 mole), $CaCO_3$ (3.5 g, 0.035 mole), and N-methyl-N-(1H-pyrrol-1-yl)amine (3.3 g, 0.035 mole). After stirring at 80° C. for three hours, the mixture was filtered, then evaporated to a solid which was eluted on a silica gel column with 5% methanol/dichloromethane via high pressure liquid chromatography to give a solid after evaporation, 4.0 g, m.p. 195°–197° C. This material was recrystallized from acetonitrile to give 2.4 g (41%) of N-methyl-N-(1H-pyrrol-1-yl)-9-β-D-ribofuranosyl-9H-purin-6-amine, m.p. 198°–199° C.

Analysis: Calculated for $C_{15}H_{18}N_6O_4$: 52.02% C; 5.24% H; 24.26% N. Found: 51.94% C; 5.18% H; 24.35% N.

EXAMPLE 18

N-(1H-pyrrol-1-yl)-N-propyl-9-β-D-ribofuranosyl-9H-purin-6-amine

To a mixture of N-propyl-N-(1H-pyrrol-1-yl)amine (4.96 g, 0.040 mole) and $CaCO_3$ (7.0 g, 0.07 mole) in 100 ml absolute ethanol was added 6-chloropurine riboside (10 g, 0.035 mole). This mixture was heated to 80° C. and stirred for six hours. The mixture was then filtered and the filtrate evaporated to yield an oil (8 g) which was eluted with 5% methanol in dichloromethane on a silica gel column via high pressure liquid chromatography. The desired fractions were evaporated to yield a solid (2.8 g). This material was recrystallized from acetonitrile/ether/hexane (1:10:3) and the resulting crystals collected to yield 1.0 g (8%) of N-(1H-pyrrol-1-yl)-N-propyl-9-β-D-ribofuranosyl-9H-purin-6-amine, m.p. 136°–138° C.

Analysis: Calculated for $C_{17}H_{22}N_6O_4$: 54.54% C; 5.92% H; 22.45% N. Found: 54.68% C; 5.79% H; 22.52% N.

We claim:

1. A N-heteroaryl-purin-6-amine of the formula

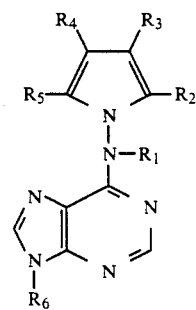

where $R_1$ is hydrogen, lower alkyl, and arylloweralkyl of the formula

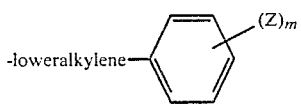

where Z is hydrogen, halogen, loweralkyl, loweralkoxy, $CF_3$, $NO_2$ and $NH_2$ and m is an integer of 1 to 3; $R_2$ and $R_3$ are independently hydrogen, loweralkyl or $R_2$ and $R_3$ taken together are aryl of the formula

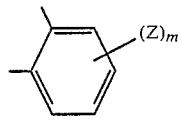

where Z and m are as defined above; $R_4$ and $R_5$ are independently hydrogen, loweralkyl or $R_4$ and $R_5$ taken together are aryl of the formula

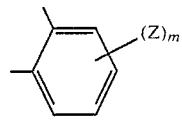

where Z and m are as defined above; $R_6$ is hydrogen, lower alkyl, aryl of the formula

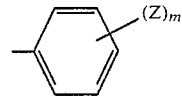

where Z and m are as defined above; arylloweralkyl of the formula

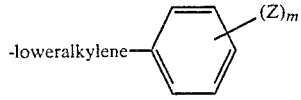

where Z and m are as defined above;

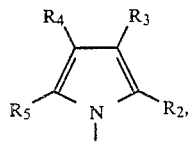

where $R_2$, $R_3$, $R_4$ and $R_5$ are as defined above, and the pharmaceutically acceptable acid addition salts thereof and where applicable the geometric and optical isomers and racemic mixtures thereof.

2. The compound as defined in claim 1 wherein $R_1$ is hydrogen, $R_2$ and $R_3$ are independently hydrogen, or taken together are aryl; $R_4$ and $R_5$ are hydrogen; $R_6$ is hydrogen,

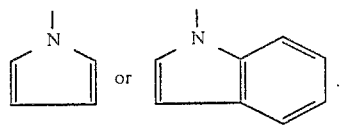

3. The compound as defined in claim 1 which is N-(3-methyl-1H-indol-1-yl)-9H-purin-6-amine and the pharmaceutically acceptable addition salts thereof.

4. The compound as defined in claim 1 which is N-(1H-pyrrol-1-yl)-9H-purin-6-amine and the pharmaceutically acceptable addition salts thereof.

5. The compound as defined in claim 1 which is N-(9H-purin-6-yl)-9H-cabazol-9-amine and the pharmaceutically acceptable addition salts thereof.

6. The compound as defined in claim 1 which is N-benzyl-N-(1H-pyrrol-1-yl)-9H-purin-6-amine and the pharmaceutically acceptable addition salts thereof.

7. The compound as defined in claim 1 which is N-methyl-N-(1H-pyrrol-1-yl)-9H-purin-6-amine and the pharmaceutically acceptable addition salts thereof.

8. The compound as defined in claim 1 which is N-propyl-N-(1H-pyrrol-1-yl)-9H-purin-6-amine and the pharmaceutically acceptable addition salts thereof.

9. The compound as defined in claim 1 which is 9-(2-fluorobenzyl)-N-(1H-indol-1-yl)-9H-purin-6-amine and the pharmaceutically acceptable addition salts thereof.

10. The compound as defined in claim 1 which is N-(1H-indol-1-yl)-N-propyl-9H-purin-6-amine and the pharmaceutically acceptable addition salts thereof.

11. The compound as defined in claim 1 which is 6-chloro-9-(1H-pyrrol-1-yl)-9H-purine and the pharmaceutically acceptable addition salts thereof.

12. The compound as defined in claim 1 which is 9-(1H-pyrrol-1-yl)-N-(1H-pyrrol-1-yl)-9H-purin-6-amine and the pharmaceutically acceptable addition salts thereof.

13. The compound as defined in claim 1 which is 9-(2-fluorobenzyl)-N-(1H-pyrrol-1-yl)-9H-purin-6-amine and the pharmaceutically acceptable addition salts thereof.

14. The compound as defined in claim 1 which is 9-(2-fluorobenzyl)-N-methyl-N-(1H-pyrrol-1-yl)-9H-purin-6-amine and the pharmaceutically acceptable addition salts thereof.

15. The compound as defined in claim 1 which is 9-(1H-indol-1-yl)-N-(1H-indol-1-yl)-9H-purin-6-amine and the pharmaceutically acceptable addition salts thereof.

16. An analgesic composition which comprises an effective pain alleviating amount of a compound of the formula

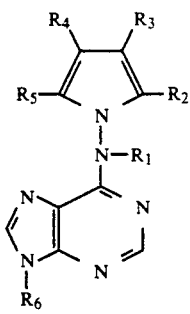

where R₁ is hydrogen, lower alkyl, and arylloweralkyl of the formula

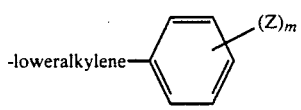

where Z is hydrogen, halogen, loweralkyl, loweralkoxy, CF₃, NO₂ and NH₂ and m is an integer of 1 to 3; R₂ and R₃ are independently hydrogen, lower alkyl or R₂ and R₃ taken together are aryl of the formula

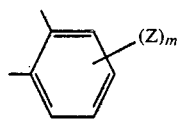

where Z and m are as defined above; R₄ and R₅ are independently hydrogen, lower alkyl or R₄ and R₅ taken together are aryl of the formula

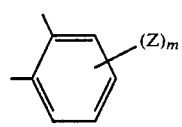

where Z and m are as defined above; R₆ is hydrogen, lower alkyl, aryl of the formula

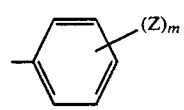

where Z and m are as defined above; arylloweralkyl of the formula

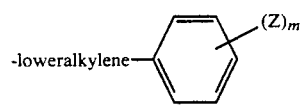

where Z and m are as defined above;

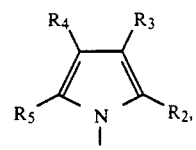

where R₂, R₃, R₄ and R₅ are as defined above, and the pharmaceutically acceptable acid addition salts thereof and where applicable the geometric and optical isomers and racemic mixtures thereof; and a suitable carrier therefor.

17. The composition as defined in claim 16 wherein R₁ is hydrogen; R₂ and R₃ are independently hydrogen or taken together are aryl; R₄ and R₅ are hydrogen; R₆ is hydrogen,

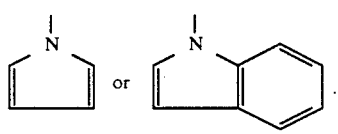

18. The composition as defined in claim 16 which comprises
N-(3-methyl-1H-indol-1-yl)-9H-purin-6-amine and the pharmaceutically acceptable addition salts thereof.

19. The composition as defined in claim 16 which comprises
N-(1H-pyrrol-1-yl)-9H-purin-6-amine and the pharmaceutically acceptable addition salts thereof.

20. The composition as defined in claim 16 which comprises
N-(9H-purin-6-yl)-9H-cabazol-9-amine and the pharmaceutically acceptable addition salts thereof.

21. The composition as defined in claim 16 which comprises
N-benzyl-N-(1H-pyrrol-1-yl)-9H-purin-6-amine and the pharmaceutically acceptable addition salts thereof.

22. The composition as defined in claim 16 which comprises
N-methyl-N-(1H-pyrrol-1-yl)-9H-purin-6-amine and the pharmaceutically acceptable addition salts thereof.

23. The composition as defined in claim 16 which comprises
N-propyl-N-(1H-pyrrol-1-yl)-9H-purin-6-amine and the pharmaceutically acceptable addition salts thereof.

24. The composition as defined in claim 16 which comprises
9-(2-fluorobenzyl)-N-(1H-indol-1-yl)-9H-purin-6-amine and the pharmaceutically acceptable addition salts thereof.

25. The composition as defined in claim 16 which comprises
N-(1H-indol-1-yl)-N-propyl-9H-purin-6-amine and the pharmaceutically acceptable addition salts thereof.

26. The composition as defined in claim 16 which comprises
6-chloro-9-(1H-pyrrol-1-yl)-9-purine and the pharmaceutically acceptable addition salts thereof.

27. The composition as defined in claim 16 which comprises
9-(1H-pyrrol-1-yl)-N-(1H-pyrrol-1-yl)-9H-purin-6-amine and the pharmaceutically acceptable addition salts thereof.

28. The composition as defined in claim 16 which comprises
9-(2-fluorobenzyl)-N-(1H-pyrrol-1-yl)-9H-purin-6-amine and the pharmaceutically acceptable addition salts thereof.

29. The composition as defined in claim 16 which comprises
9-(2-fluorobenzyl)-N-methyl-N-(1H-pyrrol-1-yl)-9H-purin-6-amine and the pharmaceutically acceptable addition salts thereof.

30. The composition as defined in claim 16 which comprises
9-(1H-indol-1-yl)-N-(1H-indol-1-yl)-9H-purin-6-amine and the pharmaceutically acceptable addition salts thereof.

31. An anticonvulsant pharmaceutical composition which comprises an anticonvulsant effective amount of a compound having the formula

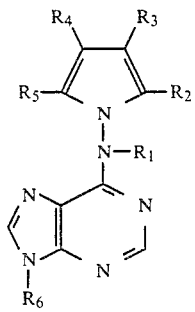

where $R_1$ is hydrogen, lower alkyl, and arylloweralkyl of the formula

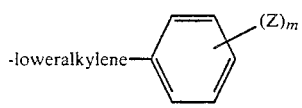

where Z is hydrogen, halogen, loweralkyl, loweralkoxy, $CF_3$, $NO_2$ and $NH_2$ and m is an integer of 1 to 3; $R_2$ and $R_3$ are independently hydrogen, lower alkyl or $R_2$ and $R_3$ taken together are aryl of the formula

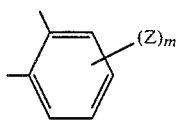

where Z and m are as defined above; $R_4$ and $R_5$ are independently hydrogen, lower alkyl or $R_4$ and $R_5$ taken together are aryl of the formula

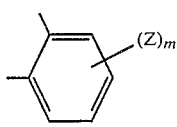

where Z and m are as defined above; $R_6$ is hydrogen, lower alkyl, aryl of the formula

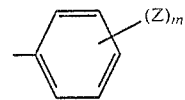

where Z and m are as defined above; arylloweralkyl of the formula

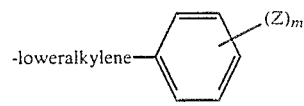

where Z and m are as defined above;

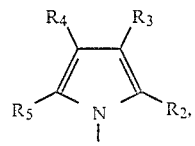

where $R_2$, $R_3$, $R_4$, $R_5$ are as previously defined above, and the pharmaceutically acceptable acid addition salts thereof and where applicable the geometric and optical isomers and racemic mixtures thereof; and a pharmaceutically acceptable carrier thereof.

32. The composition as defined in claim 31 wherein $R_1$ is hydrogen, $R_2$ and $R_3$ are hydrogen or taken together are aryl; $R_4$ and $R_5$ are hydrogen; $R_6$ is hydrogen,

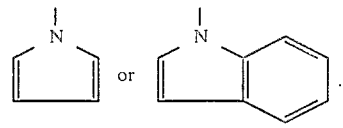

33. The composition as defined in claim 31 which comprises
N-(3-methyl-1H-indol-1-yl)-9H-purin-6-amine and the pharmaceutically acceptable addition salts thereof.

34. The composition as defined in claim 31 which comprises
N-(1H-pyrrol-1-yl)-9H-purin-6-amine and the pharmaceutically acceptable addition salts thereof.

35. The composition as defined in claim 31 which comprises
N-(9H-purin-6-yl)-9H-cabazol-9-amine and the pharmaceutically acceptable addition salts thereof.

36. The composition as defined in claim 31 which comprises
N-benzyl-N-(1H-pyrrol-1-yl)-9H-purin-6-amine and the pharmaceutically acceptable addition salts thereof.

37. The composition as defined in claim 31 which comprises
N-methyl-N-(1H-pyrrol-1-yl)-9H-purin-6-amine and the pharmaceutically acceptable addition salts thereof.

38. The composition as defined in claim 31 which comprises
N-propyl-N-(1H-pyrrol-1-yl)-9H-purin-6-amine and the pharmaceutically acceptable addition salts thereof.

39. The composition as defined in claim 31 which comprises 9-(2-fluorobenzyl)-N-(1H-indol-1-yl)-9H-purin-6-amine and the pharmaceutically acceptable addition salts thereof.

40. The composition as defined in claim 31 which comprises
N-(1H-indol-1-yl)-N-propyl-9H-purin-6-amine and the pharmaceutically acceptable addition salts thereof.

41. The composition as defined in claim 31 which comprises
6-chloro-9-(1H-pyrrol-1-yl)-9H-purine and the pharmaceutically acceptable addition salts thereof.

42. The composition as defined in claim 31 which comprises
9-(1H-pyrrol-1-yl)-N-(1H-pyrrol-1-yl)-9H-purin-6-amine and the pharmaceutically acceptable addition salts thereof.

43. The composition as defined in claim 31 which comprises
9-(2-fluorobenzyl)-N-(1H-pyrrol-1-yl)-9H-purin-6-amine and the pharmaceutically acceptable addition salts thereof.

44. The composition as defined in claim 31 which comprises
9-(2-fluorobenzyl)-N-methyl-N-(1H-pyrrol-1-yl)-9H-purin-6-amine and the pharmaceutically acceptable addition salts thereof.

45. The composition as defined in claim 31 which comprises
9-(1H-indol-1-yl)-N-(1H-indol-1-yl)-9H-purin-6-amine and the pharmaceutically acceptable addition salts thereof.

46. A method of alleviating pain in a mammal which comprises administering to a mammal a pain alleviating effective amount of a compound having the formula

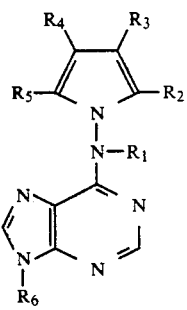

where $R_1$ is hydrogen, lower alkyl, and arylloweralkyl of the formula

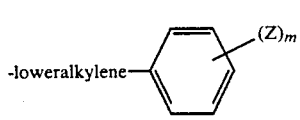

where Z is hydrogen, halogen, loweralkyl, loweralkoxy, $CF_3$, $NO_2$ and $NH_2$ and m is an integer of 1 to 3; $R_2$ and $R_3$ are independently hydrogen, loweralkyl or $R_2$ and $R_3$ taken together are aryl of the formula

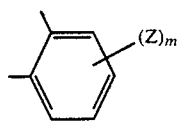

where Z and m are as defined above; $R_4$ and $R_5$ are independently hydrogen, loweralkyl or $R_4$ and $R_5$ taken together are aryl of the formula

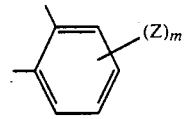

where Z and m are as defined above; $R_6$ is hydrogen, lower alkyl, aryl of the formula

where Z and m are as defined above; arylloweralkyl of the formula

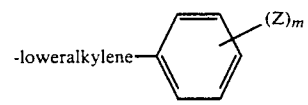

where Z and m are as defined above;

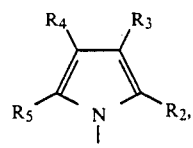

where $R_2$, $R_3$, $R_4$ and $R_5$ are as previously defined, and the pharmaceutically acceptable acid addition salts thereof and where applicable the geometric and optical isomers and racemic mixtures thereof.

47. A method of treating convulsions in a mammal which comprises administering to a mammal an anticonvulsant effective amount of a compound having the formula

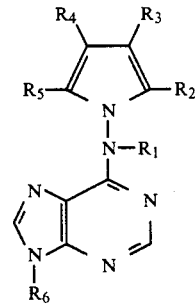

where $R_1$ is hydrogen, lower alkyl, and arylloweralkyl of the formula

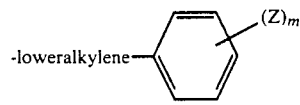

where Z is hydrogen, halogen, loweralkyl, loweralkoxy, $CF_3$, $NO_2$ and $NH_2$ and m is an integer of 1 to 3; $R_2$ and $R_3$ are independently hydrogen, loweralkyl or $R_2$ and $R_3$ taken together are aryl of the formula

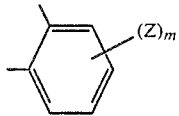

where Z and m are as defined above; $R_4$ and $R_5$ are independently hydrogen, loweralkyl or $R_4$ and $R_5$ taken together are aryl of the formula

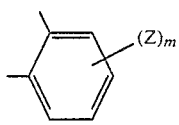

where Z and m are as defined above; $R_6$ is hydrogen, lower alkyl, aryl of the formula

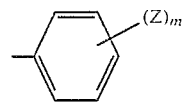

where Z and m are as defined above; arylloweralkyl of the formula

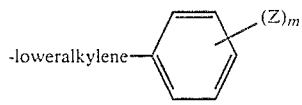

where Z and m are as defined above;

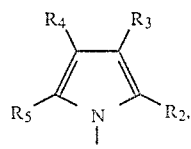

where $R_2$, $R_3$, $R_4$ and $R_5$ are as previously defined, and the pharmaceutically acceptable acid addition salts thereof and where applicable the geometric and optical isomers and racemic mixtures thereof.

* * * * *